United States Patent [19]
Schradi et al.

[11] Patent Number: 5,860,918
[45] Date of Patent: Jan. 19, 1999

[54] REPRESENTATION OF A REVIEW OF A PATENT'S PHYSIOLOGICAL PARAMETERS

[75] Inventors: Thomas Schradi, Rutesheim; Gerhard Tivig, Boeblingen, both of Germany

[73] Assignee: Hewlett-Packard Company, Palo Alto, Calif.

[21] Appl. No.: 845,176

[22] Filed: Apr. 21, 1997

Related U.S. Application Data

[63] Continuation-in-part of Ser. No. 755,064, Nov. 22, 1996, abandoned.

[51] Int. Cl.$^6$ .................................................. A61B 5/00
[52] U.S. Cl. ................................... 600/300; 600/523
[58] Field of Search ............................... 600/300, 301, 600/323, 513, 515, 516, 517, 519, 523, 525, 544, 545; 128/920–925

[56] References Cited

U.S. PATENT DOCUMENTS

| | | | |
|---|---|---|---|
| 5,047,930 | 9/1991 | Martens et al. | 600/301 |
| 5,189,609 | 2/1993 | Tivig et al. . | |
| 5,262,944 | 11/1993 | Weisner et al. . | |
| 5,447,164 | 9/1995 | Shaya et al. | 600/513 |
| 5,520,176 | 5/1996 | Cohen | 600/300 |

*Primary Examiner*—Jennifer Bahr
*Assistant Examiner*—Eric F. Winakur

[57] ABSTRACT

A medical monitoring device includes a system for monitoring and recording physiological parameters of a patient. The monitored physiological parameters are compared by a comparator with a predetermined threshold or an alarm limitassociated with the respective physiological parameter, the presence of an event being detected, if a physiological parameter exceeds the associated threshold or the associated alarm limit for a predetermined period of time, depending on an operation mode set by a user. If the presence of an event is detected, the fact that an event was detected, the parameter value which caused the event and, optionally, further recorded parameter values as well as the respective time at which the event was detected are stored in a memory. Finally, the medical monitoring device includes a display on which a representation of the events which were stored during a predetermined, preceding period of time is produced in relation to time. The mode of representation of a respective event depends on the extent to which the parameter causing the event has exceeded the associated threshold or the associated alarm limit. Alternatively or additionally, the representation also contains a display showing the respective thresholds during said predetermined period of time, in relation to time.

19 Claims, 7 Drawing Sheets

Memory Overflow - old events are overwritten

REPRESENTATION OF A REVIEW OF A PATENT'S PHYSIOLOGICAL PARAMETERS

RELATED APPLICATION

This application is a continuation in part of application of Ser. No. 08/755,064, filed Nov. 22, 1996 now abandoned.

FIELD OF THE INVENTION

The present invention refers to a system for monitoring and representing physiological parameters of a patient and, in particular, to a representation of a review of one or of a plurality of physiological parameters which have been recorded during a predetermined, preceding period of time.

DESCRIPTION OF THE PRIOR ART

When patients are medically monitored, representations of reviews, so-called trends, are used for representing physiological parameters of a patient over a considerable period of time, e.g. several hours. For such representations, the detected data concerning the parameters must, of course, be compressed, whereby diagnostic information gets lost. The loss of this diagnostic information is not critical in most cases, since the person carrying out the medical monitoring, e.g. the physician, does not even need this information. If, however, a clinical event occurs, e.g. bradycardia, i.e. a significant decrease in the heart rate, there must be a possibility of making the non-compressed and stored data in the temporal surroundings of this event, i.e. of the clinical event, available to the physician. For this reason, the time at which the event occurred is marked in the review or trend representation, and the real time data obtained by the monitoring and surrounding the event are stored. This enables the physician to have the real time data associated with an event imported later on and to observe in this way the parameter behaviour in the surroundings of this event, e.g. by moving a cursor to the point where the event is marked in the trend representation and by selecting the event by means of clicking on.

In the known review or trend representations, the occurrence of events is plotted along a time axis, an event indicating that a physiological parameter has exceeded a predetermined threshold. These known review representations contain information on the number of events which occurred at a specific time as well as on the severity of said events.

The trend representations according to the prior art are disadvantageous insofar as they offer to a user, who uses the trend representation for the medical diagnosis of the condition of a patient, only insufficient information with regard to the events that occurred during the preceding period of time.

SUMMARY OF THE INVENTION

It is an object of the present invention to provide devices and methods for producing representations of reviews of a patient's physiological parameters, said review representations permitting a user to make detailed statements with regard to events that occurred during the period of time covered by the respective review representation.

In accordance with a first aspect of the invention, this object is achieved by a medical monitoring device comprising:

a means for monitoring and recording at least one physiological parameter of a patient;

a means for comparing at least one monitored physiological parameter with a predetermined threshold or an alarm limit associated with the respective physiological parameter, and for detecting the presence of an event, if a physiological parameter exceeds the associated threshold or the associated alarm limit for a predetermined period of time;

a means for storing the fact that an event was detected and the parameter value which caused the event, or the parameter value which caused the event and further recorded parameter values, and the respective time at which the event was detected; and a means for producing a representation of the events, which were stored during a predetermined, preceding period of time, in relation to time, the mode of representation of a respective event depending on the extent to which the parameter causing the event has exceeded the associated threshold or the associated alarm limit.

The event condition is either the occurance of an alarm, for an "alarm triggered" parameter, if the physiological parameter exceeds the associated alarm limits for a predetermined period of time, or the fact that a physiological parameter exceeds for a predetermined period of time the threshold associated therewith, for a "threshold triggered" parameter.

In accordance with a preferred embodiment of the present invention, the storage means stores in response to the occurrence of an event the physiological parameter or the plurality of physiological parameters in a predetermined time window before and after the time at which an event has been detected, and wherein the mode of representation of the events depends on the maximum extent to which the parameter causing an event has exceeded the associated threshold or the associated alarm limit within said time window.

In accordance with another preferred embodiment of the present invention, the events are shown in the representation by vertical bars over a horizontal time axis, the length of the bars depending on the extent to which the parameter which caused an event exceeded the associated threshold or the associated alarm limit.

In a further preferred embodiment of the present invention, the representation additionally includes a display showing the respective thresholds or alarm limits during the predetermined, preceding period of time in relation to time. Further, the representation for each physiological parameter comprises a coordinate system on the first time axis of which the time is shown and on the second axis of which, which extends at right angles to said first axis, a range of values of the respective physiological parameter is shown, the threshold or alarm limit associated with the respective physiological parameter being shown as a curve in said coordinate system, and the events being shown in the form of vertical bars in said coordinate system, the length of said bars depending on the maximum extent to which the physiological parameter which caused an event has exceeded the associated threshold or the associated alarm limit.

In accordance with a second aspect of the invention, this object is achieved by a medical monitoring device comprising:

a means for monitoring and recording at least one physiological parameter of a patient;

a means for comparing at least one monitored physiological parameter with a predetermined threshold or an alarm limit associated with the respective physiological parameter, and for detecting the presence of an event, if a physiological parameter exceeds the associated threshold or alarm limit for a predetermined period of time;

a means for storing the fact that an event was detected and the parameter value which caused the event, or the parameter value which caused the event and further recorded parameter values, and the respective time at which the event was detected; and a means for producing a representation of the events, which were stored during a predetermined, preceding period of time, in relation to time, the representation additionally containing a display showing the respective thresholds or alarm limits during said predetermined period of time, in relation to time.

In accordance with a third aspect of the invention, this object is achieved by a method for medical monitoring comprising the steps of:

monitoring and recording at least one physiological parameter of a patient;

comparing at least one monitored physiological parameter with a predetermined threshold or an alarm limit associated with the respective physiological parameter, and detecting the presence of an event, if a physiological parameter exceeds the associated threshold or the associated alarm limit for a predetermined period of time;

storing the fact that an event was detected and the parameter value which caused the event, or the parameter value which caused the event and further recorded parameter values, and the respective time at which the event was detected; and producing a representation of the events, which were stored during a predetermined, preceding period of time, in relation to time, the mode of representation of a respective event depending on the extent to which the parameter causing the event has exceeded the associated threshold or the associated alarm limit.

In accordance with a fourth aspect of the invention, this object is achieved by a method for medical monitoring comprising the steps of:

monitoring and recording at least one physiological parameter of a patient;

comparing at least one monitored physiological parameter with a predetermined threshold or an alarm limit associated with the respective physiological parameter, and detecting the presence of an event, if a physiological parameter exceeds the associated threshold or alarm limit for a predetermined period of time;

storing the fact that an event was detected and the parameter value which caused the event, or the parameter value which caused the event and further recorded parameter values, and the respective time at which the event was detected; and producing a representation of the events, which were stored during a predetermined, preceding period of time, in relation to time, the representation additionally containing a display showing the respective thresholds or alarm limits during said predetermined period of time, in relation to time.

In preferred embodiments of all aspects of the present invention, the alarm limit can be set by a user.

The present invention provides methods and devices for displaying events in a review representation. In this review representation, the events are, on the one hand, set temporally correct and, on the other hand, their mode of representation also shows which local minimum/maximum value the respective parameter, which triggered an event, has reached. According to a further aspect of the present invention, the thresholds or alarm limits are recorded in the horizontal direction so that a user can see immediately how far the parameter exceeded the limit associated therewith, whether the limit was set to an adequate value and whether an alarm had actually been switched on. For representing the events, the present invention preferably uses vertical bars whose height depends on the extent to which a parameter, which triggered an event, exceeded the threshold or alarm limit associated therewith.

Physiological parameters which can advantageously be represented according to the present invention are e.g. the occurrence of an apnea, a bradycardia and a desaturation (low SpO2), or a combination of these parameters. These physiological parameters are used in the field of medicine for monitoring the condition of neonates. The present invention can, for example, be used for producing a graphical review of the events which occurred within the last 24 hours and which are caused by the occurrence of an apnea, a bradycardia or a desaturation, the events being shown in the form of vertical bars, and the event thresholds or alarm limits being shown in the form of trend lines, i.e. as horizontal lines above the time axis. The occurrence of the events themselves and the number of events within a predetermined period of time, e.g. 24 hours, as well as information on the intensity and the duration of an event are relevant with regard to the condition of the patient, e.g. the neonate.

The time-correlated recording of the thresholds or alarm limits and the events during the predetermined, preceding period of time provides the user with a higher information density for diagnostic or documentational purposes. It follows that the user can, for example, see why in the preceding period of time, e.g. 24 hours, a large number or a small number of events or no events at all occurred. According to one advantage of the present invention, the threshold or alarm limit is not shown in the review representation if it was inactive for a specific period of time. This permits the user to judge the patient's condition more effectively, since thresholds or alarm limits of different channels, i.e. of different physiological parameters, may have been deactivated or changed by some other user so as to adapt said thresholds or alarm limits to a special patient or a special monitoring situation. The present invention offers the user a possibility of recognizing such changes of thresholds or alarm limits when looking at the review representation. This is advantageous especially in cases where a plurality of persons uses the monitoring device, as will normally be the case when there is shift working in a hospital.

The present invention permits the recording, storage, viewing and erasing of medical events, e.g. medical events concerning neonates. Preferably, one physiological parameter or a plurality of physiological parameters are stored during a predetermined time window, e.g. four minutes around a detected event. This permits further analyzing of each event by observing the stored episode in the time window. Furthermore, the review representation produced and the episode representation can preferably be printed out. The thresholds and further parameters, which determine the triggering of an event, can preferably be set by a user or they can be aligned wtih the parameter "alarm specification" separately for each channel. So the user can set separately for each parameter channel whether the event triggering is based on the associated threshold or linked to the associated alarm. For example, the user can decide to have Brady events triggered by an Brady alarm and Desaturation events triggered by exceeding the associated threshold.

BRIEF DESCRIPTION OF THE DRAWINGS

Preferred embodiments of the present invention will be described in detail hereinbelow making reference to the drawings enclosed, in which.

DESCRIPTION OF PREFERRED EMBODIMENTS OF THE PRESENT INVENTION

Figure 1:
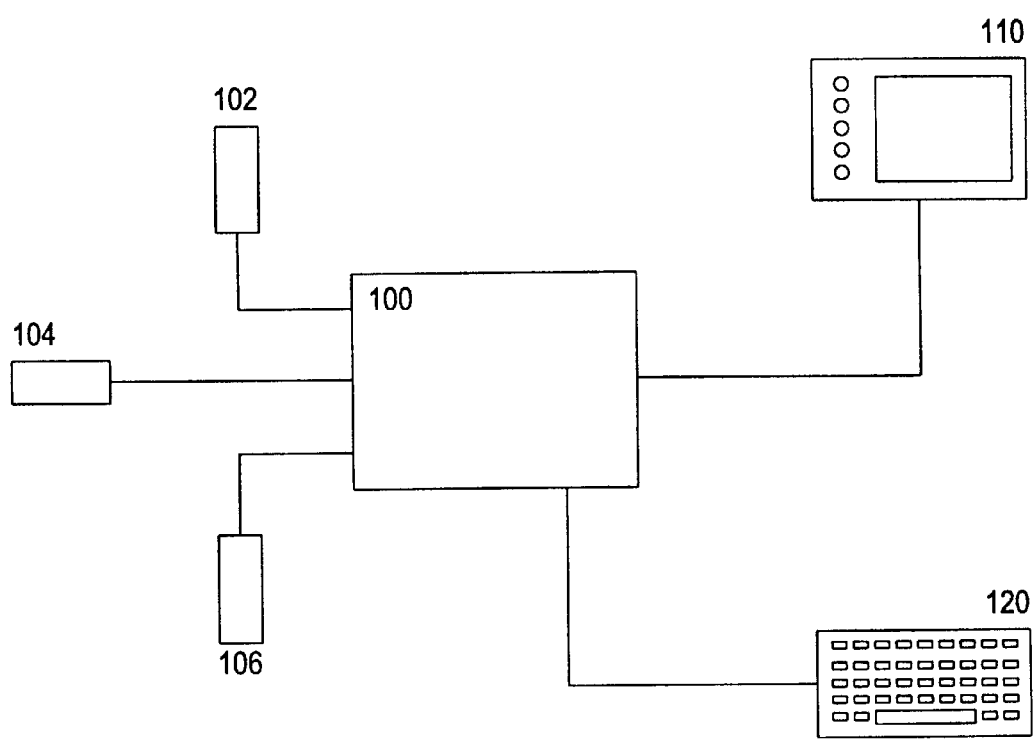
FIG. 1 shows a schematic, simplified representation of the medical monitoring device according to the present invention.

FIG. 1 shows a simplified, schematic representation of a medical monitoring device according to the present invention. The medical monitoring device comprises a central system 100. The central system 100 has coupled thereto detection devices 102, 104 and 106 for detecting and recording physiological parameters of a patient. The detection devices 102, 104 and 106 may, for example, be conventional devices for detecting the occurrence of an apnea, a bradycardia or a desaturation. These three event parameters are detected according to a preferred embodiment of the present invention. It is, however, obvious that the detection devices may also comprise devices used for detecting other physiological parameters. The device according to the present invention may additionally comprise a larger or a smaller number of detection devices than the three detection devices shown in the figure.

The central system 100 has additionally connected thereto a display device 110. The display device 110 may, for example, be a cathode-ray tube, and it serves to display the physiological parameters detected by means of the central system 100 and the detection devices 102 to 106. The central system 100 comprises all the means that are necessary for processing the signals produced by the detection devices 102 to 106 so as to permit a display of said signals on the display device 110. Means of this type, such as interfaces, memories, processors, etc., are well-known technical means.

Furthermore, the central system 100 has connected thereto an input device 120 via a user interface. The input device 120 may be a conventional input device, such as a keyboard, a control mouse, a track ball, etc., or a combination of these elements. Making use of the input device 120, a user is capable of influencing the detection of events of the physiological parameters, the comparison of said parameters with thresholds or alarm limits, and the display thereof on the display device 110.

In the following, preferred embodiments of the present invention will be explained in detail making reference to the detection of an apnea, a bradycardia and a desaturation, the detection of the above-mentioned parameter events being especially used for monitoring the condition of neonates. First of all, some of the terms used in the description following hereinbelow are briefly explained in greater detail.

The expression event as used hereinbelow refers to an occurrence in the case of which one parameter or a plurality of parameters exceed a threshold or an alarm limit associated therewith. In this connection, the expression exceed can mean that the detected value is larger than the threshold, if said threshold is an upper limit, and also that the detected value is smaller than the threshold, if said threshold is a lower limit.

The occurrence of an event depends on the patient's condition and the instantaneous threshold settings, and further on whether or not the parameter is monitored at the time in question. The conditions for the triggering of an event in dependence upon the thresholds set will be explained hereinbelow making reference to FIG. 5A to 5D.

For describing the preferred embodiments of the present invention, three events are taken into account hereinbelow. The first event is an apnea event occurring whenever cessation of breathing, i.e. a patient's respiratory standstill, exceeds a predetermined period of time. The second event is a bradycardia event which is triggered when the heart rate falls below a specified value. The third event is a desaturation event which is triggered when the oxygen saturation measured by pulse oximetry falls below a predetermined value.

The events described are stored and documented for a future review. In so doing, various event classes can be differentiated. There are single events and combined events. A single event is an event whose occurrence is not followed by another event within a predetermined time, e.g. two minutes. The event triggering the event storage is called trigger event. If within the predetermined time window after the trigger event another event, caused by some other physiological parameter, is detected, it is not treated as a new event but forms together with the trigger event a combined event. Each combined event contains always one trigger event and one or more follow-up events.

Figure 2:
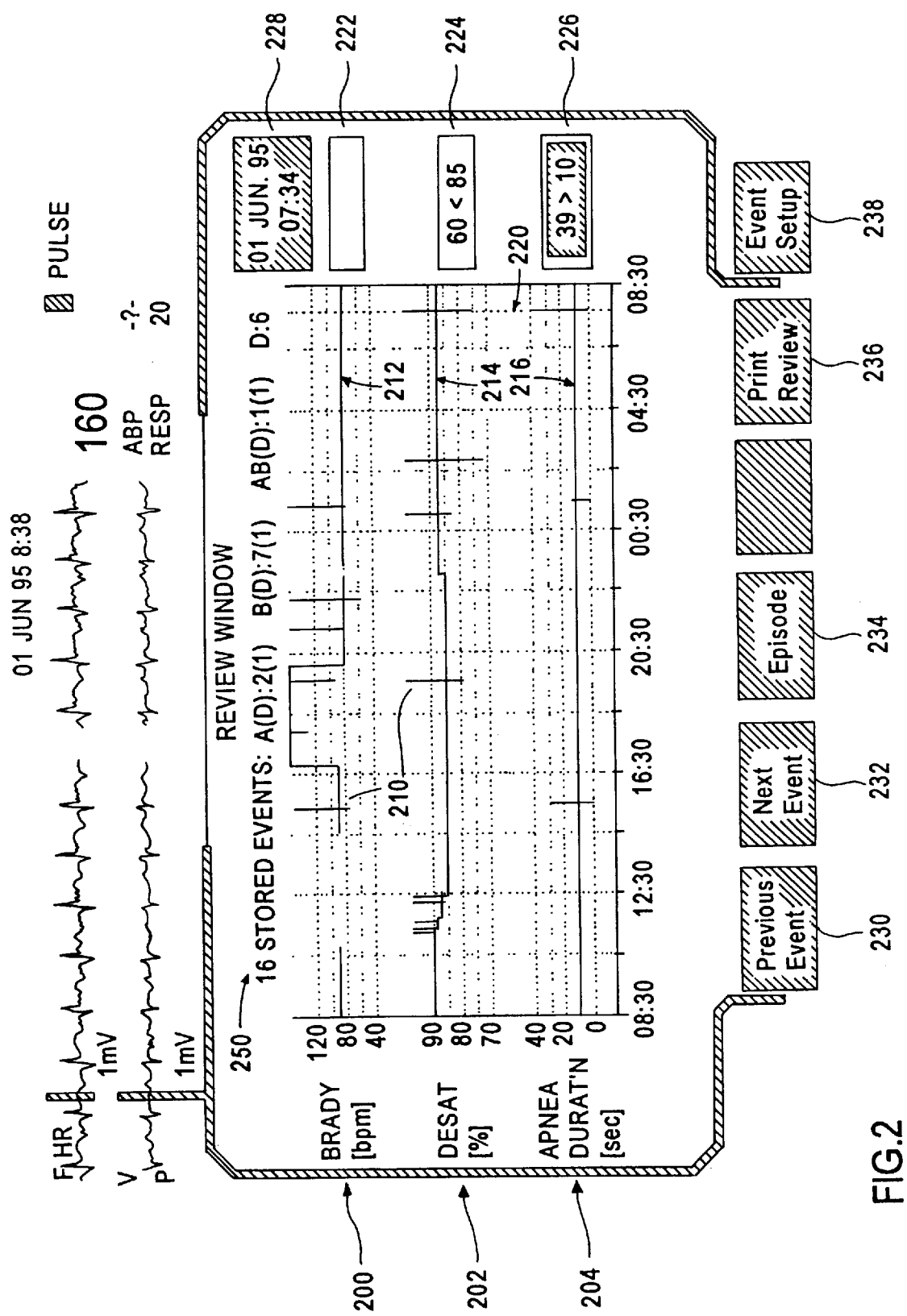
FIG. 2 shows a representation of a preferred embodiment of the review representation according to the present invention.
Figure 4:
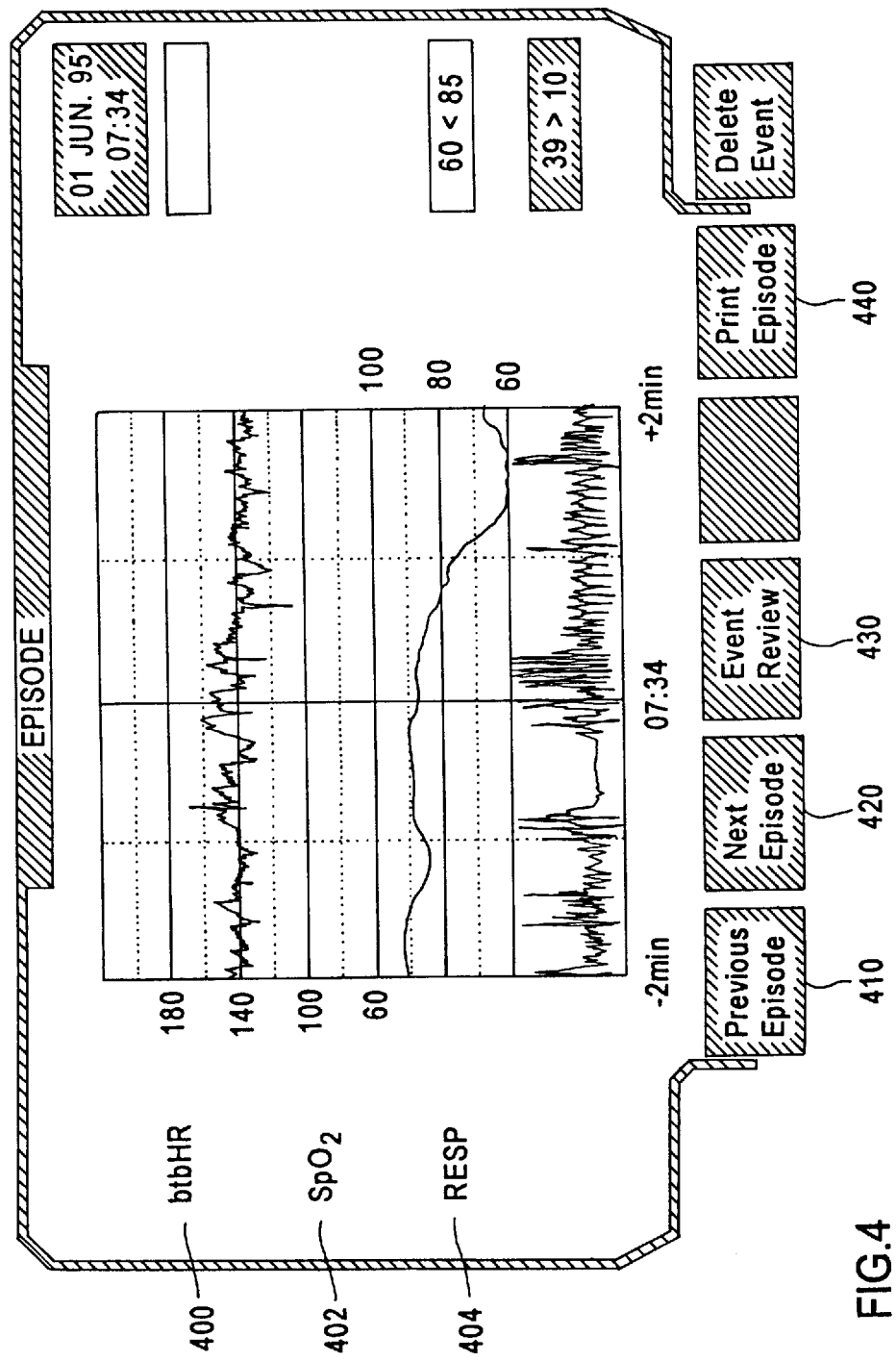
FIG. 4 shows a representation of an episode around an event.

The parameters for the triggering of an event can be adjusted by a user with the aid of the input device 120 via the user interface. The input device also permits a change-over between different windows on the display device 110. A first window is referred to as event setup window and offers the user the possibility of adjusting parameters with regard to the events and the thresholds. A second window is called event review window, the representation of this window, which is shown in FIG. 2, embodying the invention according to the present application. The input device additionally permits a change-over to a further window, as can be seen in FIG. 4, which is called episode window and which represents a time window with stored real time data of parameters in a specific time range prior to and subsequent to the detection of an event.

Making reference to FIG. 2, a preferred embodiment of the representation of a review of the patient's physiological parameters according to the present invention will be explained in detail in the following.

The representation of the review, which is called review window in the following, is displayed on the display device 110, when a user causes the central system 100 to do so via the input device 120. The review window according to the preferred embodiment contains a graphical review of the events that occurred within the last 24 hours, 08:30 to 08:30. Depending on the resources available, the maximum number of displayable events can be limited.

The review window contains three channels, one for each physiological parameter monitored: the bradycardia channel 200 has a range from 40 up to 120 bpm (bpm=beats per minute). The desaturation channel 202 has a range from 70 up to 90%. The apnea channel 204 has a range from 0 up to 40 seconds. All channels additionally contain reserved areas for values which exceed the minimum or maximum of their ranges.

As can be seen in FIG. 2, events are shown in the respective channel by vertical bars, cf. e.g. 210. The length of these bars depends on the extent to which the respective parameter, which caused an event, exceeded the threshold associated therewith. For example, the vertical bars for a bradycardia event always begin at the upper edge of the bradycardia channel and, depending on the value which the bradycardia parameter has reached, they extend downwards in the representation. The same applies to the desaturation channel where the vertical bars, which represent events, also extend from the upper edge of the desaturation channel downwards. In the apnea duration channel, the vertical bars extend from a value 0 upwards to an extent that depends on the length of the period of time during which the respiratory standstill occurred. The representation of the events in this way is one aspect of the present invention.

Another aspect of the present invention is the representation of the thresholds associated with the respective physiological parameters. In FIG. 2, the threshold associated with the bradycardia parameter is shown at 212, the threshold associated with the desaturation parameter is shown at 214 and the threshold associated with the apnea duration parameter is shown at 216. Although the representation according to FIG. 2 shows the threshold-dependent representation of the events as well as the representation of the thresholds, also a review representation containing only one of the above-mentioned options provides a user with an information bandwidth which is better than that according to the prior art.

As can be seen from FIG. 2, a user who looks at the review window is able to see immediately to what extent a parameter related to a respective event exceeded the threshold or alarm limit associated therewith. Furthermore, the user is immediately able to see which threshold or alarm limit was set for each parameter within the period of time observed. Further, the user is able to see which changes of the threshold or alarm limit occured within the period of time observed to adapt the threshold or the alarm limit to the specific patient condition to improve the system effectiveness in detecting and storing events.

In the following, further options of the review window according to the present invention will be explained.

Above the review window, specific data can be seen in FIG. 2, said data being shown on the display device of a medical monitoring device, e.g. ECG signals, the arterial blood pressure (ABP), the pulse rate (PULSE), the respiration (RESP) and the date and time of day. In the embodiment described, the review window, the setup window, or the episode window are superimposed on the normal display of the display device, when a user chooses one of these window options by means of the input device.

A cursor, which can be moved across the review window from one event to another one by a user by means of the input device 120, is designated by reference numeral 220 in FIG. 2. By means of said cursor 220, the user can choose the events shown in the review window. For example, the cursor 220 can be moved to the left and to the right by means of the directional keys on a keyboard; when the leftward-arrow directional key on the keyboard is actuated, the cursor 220 jumps to the next event on the left-hand side of the chosen event. The brightness of the cursor 220 is preferably chosen such that the event bars selected by said cursor are still visible.

If an event is selected by the cursor 220, additional information concerning the event appears in the review window of the preferred embodiment. Event string boxes 222, 224 and 226 in the right margin of the review window of the preferred embodiment contain items of information on an event bar selected by the cursor 220. The items of information have the form XXX<YYY or XXX>YYY, XXX indicating the maximum value by which the parameter has been exceeded, and YYY indicating the active threshold or alarm limit of the parameter in question. If the event selected is a combined event, the respective information appears in the string boxes of the trigger event and of the follow-up events, cf. e.g. 226 and 224. The user can immediately see, which event was the trigger event, because the trigger event is always shown "invers video" and the following events are shown in "normal video". In a field 228, information with regard to the date and the time of a selected event is shown.

In the lower area of the review window, input fields are shown by means of which a user can choose different options. By means of the field "Previous Event" 230, a user can place the cursor 220 on the event which temporally preceded the instantaneously chosen event and select said preceding event in this way. By means of the field "Next Event" 232, the user can select the next event with the aid of the cursor 220. By means of the field "Episode" 234, the user can call a time window, the so-called episode window, of the instantaneously chosen event, as will be explained in detail hereinbelow making reference to FIG. 4. By means of the field "Print Review" 236, the user can print out the instantaneously shown review window with the aid of a printer connected to the central system 100. By means of the field "Event Setup" 238, the user can enter a menu in which he can set individually for each parameter whether the event triggering should be based on the associated threshold, which also can be set in this menu, or should be linked to the occurance of the associated parameter alarm.

As can be seen in FIG. 2, the review window according to a preferred embodiment of the present invention additionally contains an event summary display 250 containing information with regard to the number of events stored within the last 24 hours in the event buffer. This display 250 additionally contains information indicating how many events of each category are contained in the event buffer. The term "A(D):2(1)" says that two apnea events occurred during the last 24 hours and that one of said apnea events occurred in combination with a desaturation. The term "B(D): 7(1)" says that a total of seven bradycardia events occurred in the last 24 hours and that one of said bradycardia events occurred in combination with a desaturation. The term AB(D): 1(1)" says that a total of one combined apnea and bradycardia event occurred during the last 24 hours and that said combined apnea and bradycardia event occurred together with a desaturation. The term "D: 6" says that a total of six isolated desaturation events occurred within the last 24 hours. The total number of stored events is, consequently, 2+7+1+6=16. This event summary display 250 is updated whenever the review window is re-entered. In the same way, the whole review window is automatically updated whenever a new event is detected and the review window has been called before, or whenever events are deleted because they fall out of memory as they are older than 24 hours and the review window has been called before.

Making reference to FIG. 3A and 3B, special options of further preferred embodiments of the review representation according to the present invention will be explained in detail.

Figure 3A:
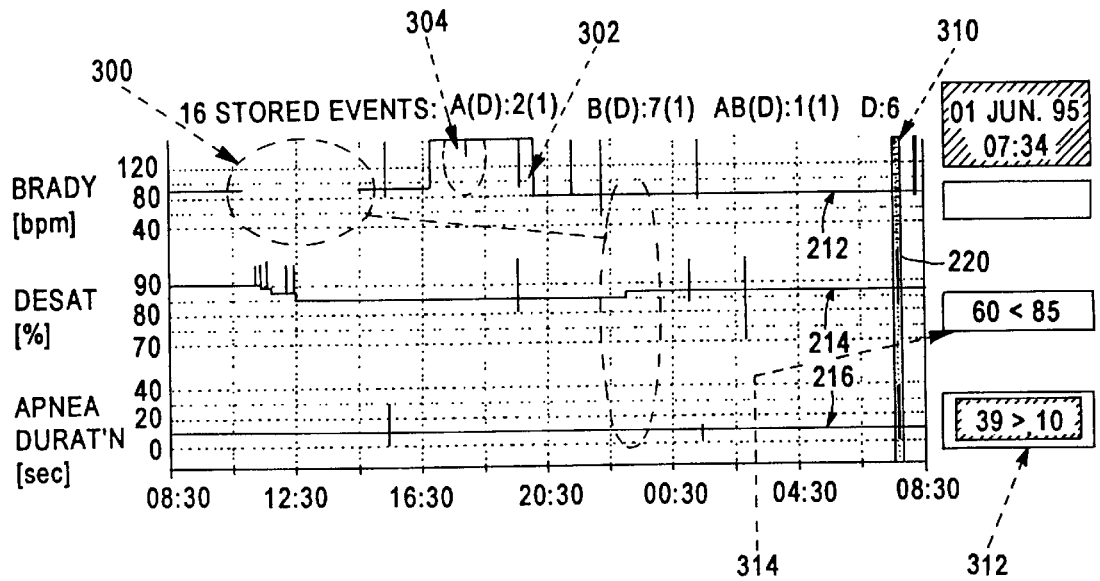
FIG. 3A and 3B show details of the review representation according to the present invention.

In FIG. 3A interruptions of the respective representations of the thresholds 212, 214 and 216 are marked by dashed-line frames and designated by reference numeral 300. Such interruptions of the threshold representation show that the respective threshold was not active during the time of interruption of the representation.

At 302, a case is shown where the threshold is above the channel range (e.g. a bradycardia threshold of 135 bpm); hence, the representation of the threshold is "clamped" at the upper edge of the range of the bradycardia channel. In the case designated by reference numeral 304, the event bar is additionally outside the channel, and this is indicative of the fact that the exceed value was also above the channel range shown (132<160).

According to the representation of FIG. 3A, the cursor 220 is arranged above a combined event, as shown at 310. If a combined event is selected, the information concerning the trigger event is always shown in inverse video in the event string box 312. The information concerning the follow-up event is shown in normal video, cf. 314.

Figure 3B:
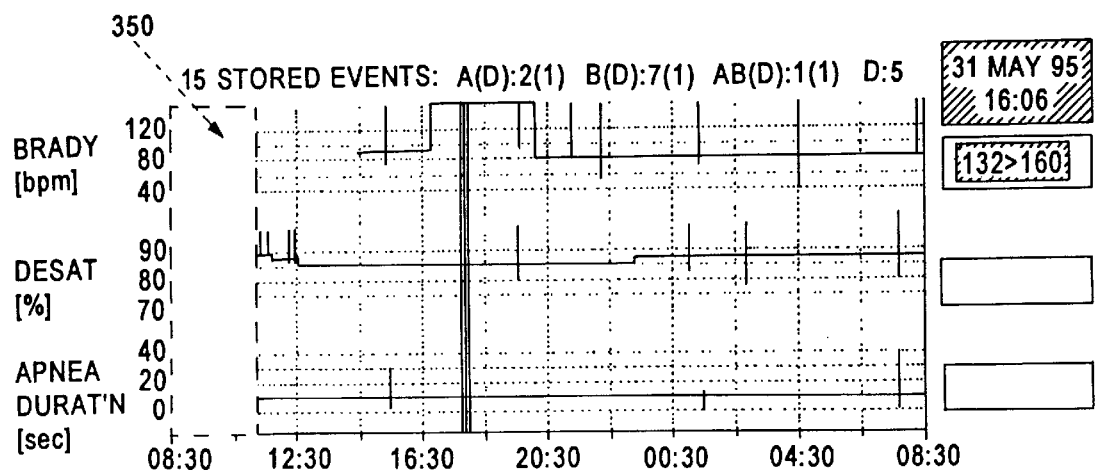

In FIG. 3B, the case is shown where old events that occurred within the last 24 hours have to be overwritten due to storage limitation, the time range from "minus 24 hours" to the time of the overwritten event being totally blanked, cf. the block outlined by a dashed line and designated by reference numeral 350. A display of the type "Memory Overflow—old events are overwritten" can then appear in the lower area of the review window so as to make known to the user that the oldest stored events are overwritten because of insufficient storage capacities. In the example shown in FIG. 3B, the capacity amounts e.g. to 15 stored events.

Time changes that might occur when switching from summer to winter time or when the monitor is (re)connected to a care network may be indicated by an inverse video question mark placed on the time scale at the time where the last change of such changes occured. All time labels left from this mark will then be preceded by a question mark because they are recalculated relative to the current time. In such a case, the event bar and time mark positioning remains unchanged and is relative to the current time. The event bar time string still contains the date and time valid at the time when the event was captured. A question mark is prefixed to denote that this time was valid before the time change occured.

In order to make the evaluation of the review representation according to the present invention easier for the user, all items of information which are assigned to one channel can, for example, be shown in one colour on the display device, whereas the items of information concerning other channels have different colours. Furthermore, the event threshold lines can be drawn with half the intensity of the event bars so as to distinguish them easier from the event bars in case of partial overlapping.

Making reference to FIG. 4, the episode window will be explained in detail hereinbelow; a user can cause the representation of said episode window on the display device by selecting an event and pressing the "episode" field in the review window. The episode window contains a representation of the recorded physiological parameters in a fixed time window around the selected event. For this purpose, the episode window of the preferred embodiment contains three channels, the graph of each physiological parameter being shown in one channel. In a first channel 400, btbHR, the patient's beat to beat heart rate is recorded. In second channel 402, Sp02, the oxygen saturation is shown, whereas in the third channel 404, RESP, the patient's respiratory activity is shown. This mode of representation permits a user to analyze a patient's condition precisely within a time range starting two minutes before a detected event and ending two minutes after said detected event. The area on the right-hand side of the episode window displays the same information with regard to the selected event as the review window.

In accordance with a preferred embodiment of the present invention, input fields by means of which a user can choose various options are again arranged in the lower area of the episode window. With the aid of the field "Previous Episode" 410, the user can switch over to a previous episode, i.e. the episode associated with the event which preceded the instantaneously chosen event. In the same way, the user can choose a subsequent episode by the field "Next Episode" 420. By means of the field "Event Review" 430, the user can go back to the representation of the review window. With the aid of the field "Print Episode" 440, the user can cause the episode window to be printed out on a printer connected to the central system.

In the following, rules for setting the thresholds and rules for triggering events will be described making reference to FIG. 5A to 5D.

An event triggering for a physiological parameter can be set such that it is linked to the alarm generation specified by its associated alarm limit. An alarm limit is the value at which a medical monitoring device triggers an optical and/or acoustical alarm so as to inform a user of the fact that an abnormal or dangerous condition of a patient exists. When the thresholds for triggering an event correspond to the alarm limit, the triggering of the event is referred to as "alarm triggered". Thresholds can, however, also be set independently of the alarm values. In such a case the triggering of an event is referred to as "threshold triggered". Whether alarm triggering or threshold triggering is to be used for a specific event parameter can be defined by the user in the above-mentioned event setup window. Preferably, apnea events are always set to "alarm triggered", whereas the triggering mode of the two other events can be selected freely. If an event is "threshold triggered", the user can specify the thresholds for different physiological parameters in the event setup window. If an event is "alarm triggered", the triggering is coupled to the alarm occurance of the associated parameter. The alarm limits of this parameter are user selectable in the parameter specific operating window.

There are so-called global event trigger conditions. A parameter must always be switched on so that an event which is related to this parameter can be triggered. Furthermore, the parameter alarm must always be switched on to trigger an event. The parameter values must have valid numerics. In addition, the device alarm must always be switched on to trigger an event.

If one condition for a parameter is not fulfilled, the threshold is invalid and the threshold trend line is blanked out on the event graph indicating that the event triggering is not active.

An event is triggered when the global event trigger conditions are fulfilled, the trigger mechanism is armed, as will be described hereinbelow, and a new event condition has occurred. The event condition is either the occurrence of an alarm for an "alarm triggered" parameter, or the fact that a physiological parameter exceeds for a given period of time the threshold associated therewith, if the threshold does not correspond to the alarm value.

Normally, the detection of an event is carried out on the basis of an average numeric value, heart rate for bradycardia or SpO2 for desaturation. An event is triggered if this average numeric value exceeds the event threshold or falls below said event threshold for a period of time given by the so-called event trigger time.

Whenever an event condition is detected, the event time and the event threshold are frozen and stored for this event. Subsequently, a time window is opened—said time window being an event window of two minutes in accordance with the preferred embodiment—so as to detect follow-up events, which form a combined event. At the same time the average numeric value is updated so as to obtain always the max-exceed value for the trigger event and the follow-up events within the window. The max-exceed value is the largest deviation of the average numeric value from the frozen threshold within the window, which is a two-minute window according to the preferred embodiment, after the trigger event.

Figure 5A:
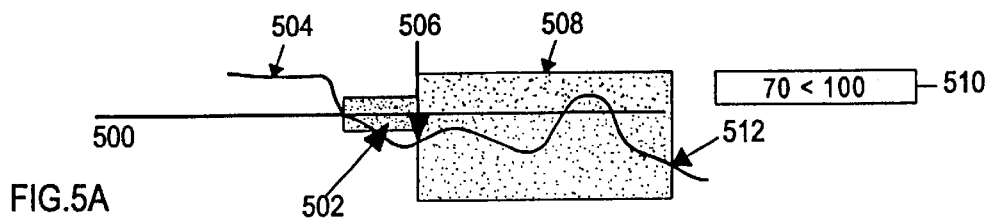
FIG. 5A to 5D show representations defining conditions for the triggering of events.

At the end of the two-minute window, an event string of the form XXX<YYY for bradycardia and desaturation events, or XXX>YYY for the apnea event, is built up and stored as associated with said event. In FIG. 5A, the triggering of the bradycardia event is shown, the threshold 500 being e.g. 100 bpm. The trigger time 502, for which the physiological parameter 504 must at least fall below the threshold 500 so that an event trigger 506 is produced, is e.g. five seconds. After the generation of the event trigger, the event window 508 is opened, said window having a length of two minutes by way of example, during which follow-up events of other physiological parameters are recorded in the case of combined events. The "event string" associated with the event is shown at 510. At 512 the detected physiological parameters 504 has the max-exceed value of 70 bpm.

At the end of the time window 508, the real time data of all of the recorded physiological parameters of a specific preceding time window are stored and associated with the recorded event, the time window of the preferred embodiment according to the present invention comprising the last four minutes. These stored real time data can be called later on by pressing the "episode" field in the review window.

Figure 5B:
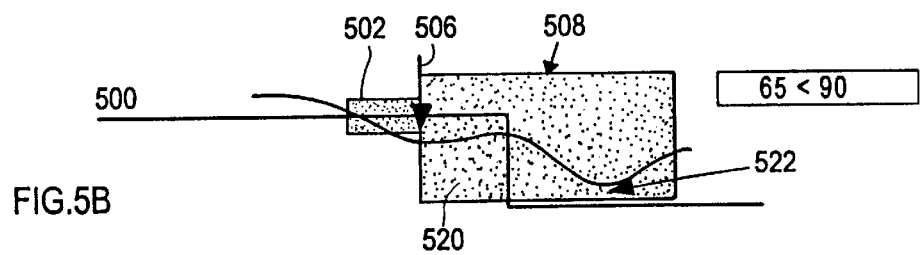

In FIG. 5B, a case is shown where the threshold 500 is changed during the event window 508, cf. 520. The change of the threshold during the event window after the trigger event does not influence the threshold used for building up the event string, i.e. a change of global event trigger conditions after the triggering of an event does not have any influence on the storage of said event. In the embodiment shown in FIG. 5B, the threshold 500 has a value of 90 bpm when the event is being triggered. After the changeover 520, the threshold has a value of e.g. 60 bpm. Although the max-exceed value 522 of the physiological parameter does not fall below the new threshold, the result is stored on the basis of the old threshold of 90 bpm, since this threshold has been frozen for the duration of the event window 508.

Figure 5C:
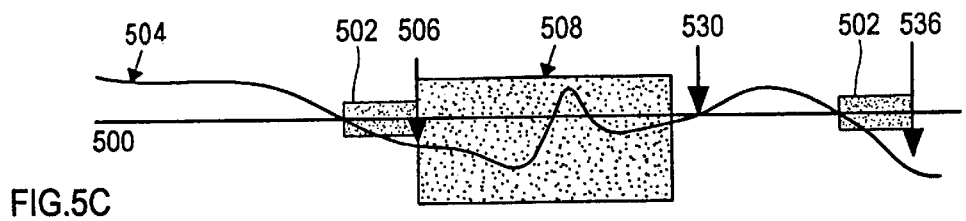

FIG. 5C shows that a new event cannot be triggered until the event window 508, which has a length of two minutes according to the preferred embodiment, has passed and the average value has exceeded the threshold 500 into the normal range, cf. point 530. At this point the trigger mechanism is armed. After the arming of the trigger mechanism, a new event 536 is triggered, if the average value falls again below the threshold 500 for at least the trigger time 502. As long as the average numeric value of the recorded physiological parameter 504 remains, however, below the threshold 500 after the end of the event window 508, no additional events are triggered with regard to this physiological parameter because the trigger mechanism is not armed.

Figure 5D:
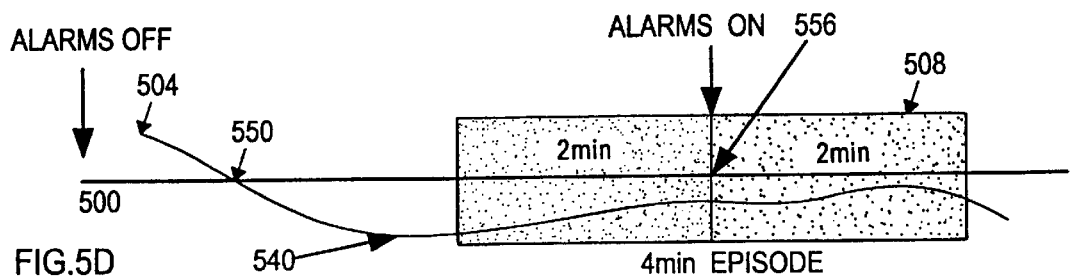

In FIG. 5D, a case is shown where the episode window, which has a length of four minutes according to the present embodiment, contains neither the max-exceed value 540 nor the passage of the physiological parameter through the threshold 500, cf. point 550. This can, for example, be the case if the alarms are switched off initially and are then switched on while the average numeric value of parameter 504 is below the threshold 500. In this case, an event trigger 556 is generated as soon as the alarms are switched on. After termination of the event window 508, the real time data of the last four minutes are stored again so as to permit the calling of the episode window later on.

Figure 6:
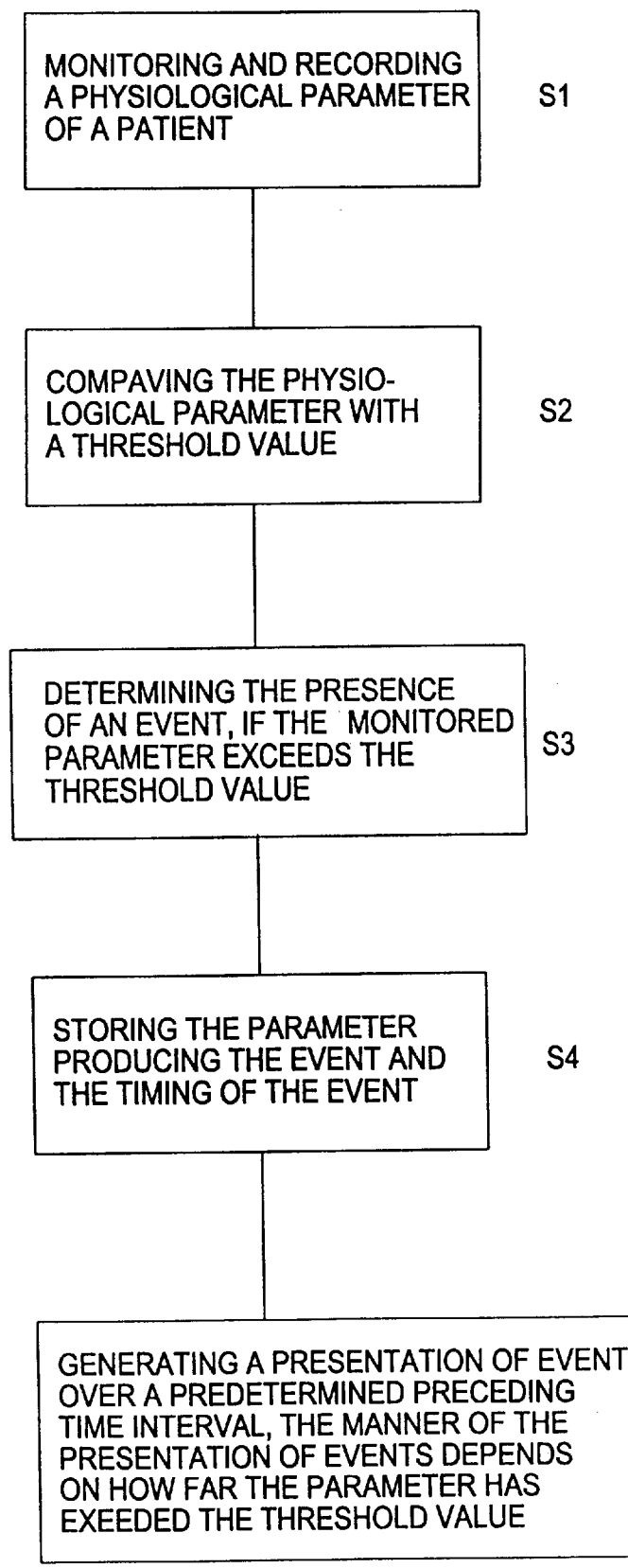
FIG. 6 shows a flow diagram of a first embodiment of the medical monitoring method according to the present invention.
Figure 7:
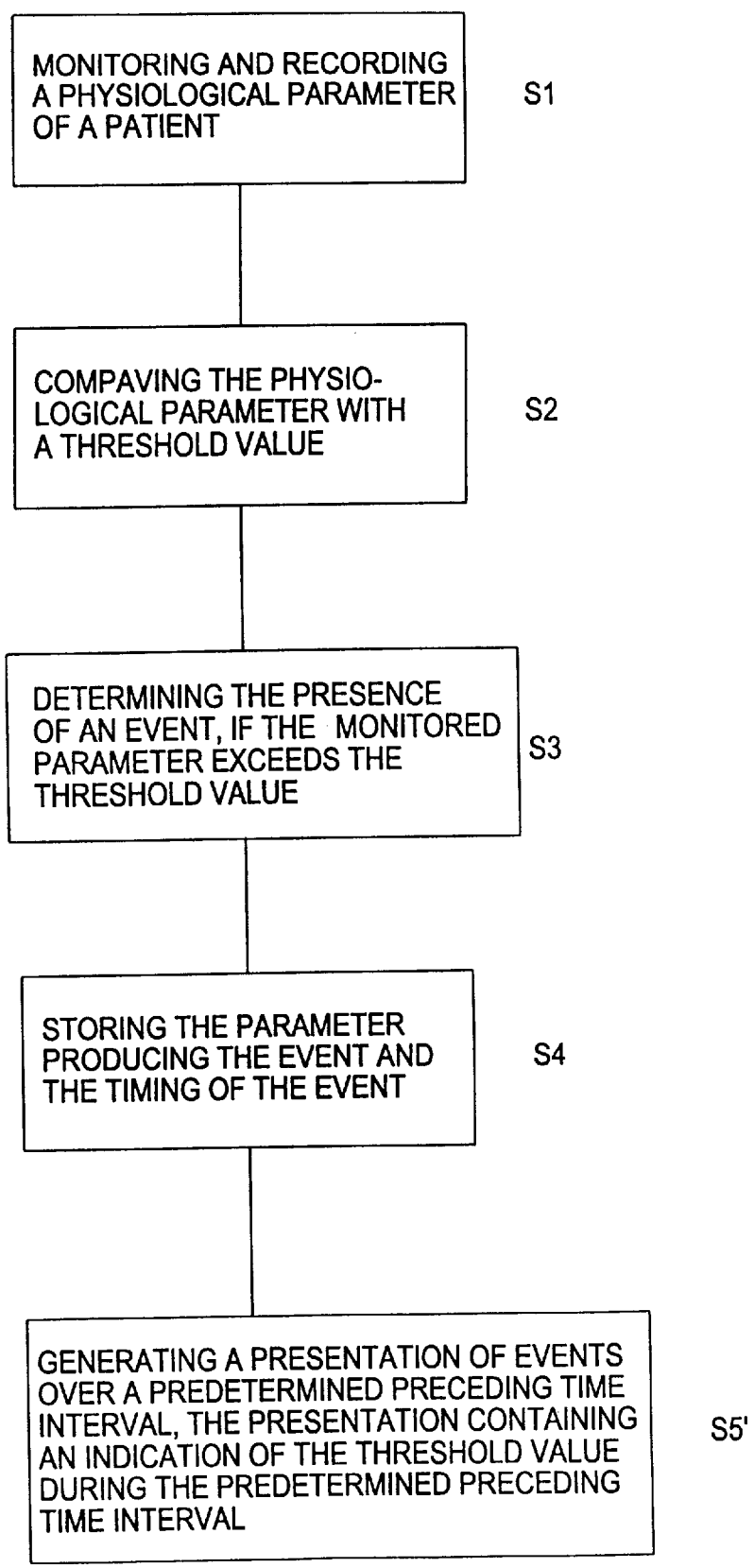
FIG. 7 shows a flow diagram of a second embodiment of the medical monitoring method according to the present invention.

FIG. 6 and 7 show simplified flow diagrams of the method according to the present invention used for medically monitoring a patient and for producing a review representation of physiological parameters of said patient. Steps S1 to S4 of the two methods are identical. In order to simplify the flow diagrams, each of said flow diagrams shows the recording of only one physiological parameter; it goes without saying that the method according to the present invention can be applied to a different number of physiological parameters.

In step S1, a physiological parameter of a patient is monitored and recorded. In step S2, said physiological parameter is compared with a threshold. If the monitored parameter exceeds the threshold, the presence of an event is determined in step S3. In step S4, the parameter causing the event and the time of the parameter are stored. It goes without saying that also the value of the threshold and changes of said threshold value caused by user inputs are stored.

In step S5, a representation of the events, which were detected during a predetermined preceding time interval, is produced in accordance with a first embodiment of the method according to the present invention, the mode of representation of the events depending on how far the parameter has exceeded the threshold in the case in question.

In accordance with an alternative embodiment of the method according to the present invention, a representation of the events, which were detected during a predetermined preceding time interval, is produced in a step S5', said representation containing a display of the threshold during said predetermined preceding time interval. It follows that the present invention provides devices and methods for producing review representations of physiological parameters of a patient, said review representations permitting the user to draw concrete conclusions with regard to the condition of a patient simply by looking at said review representation which contains the events that occurred e.g. during the last 24 hours.

If no events are present within a specific period of time, this permits conclusions with regard to the fact that the threshold was inactive, or that the threshold was set to a very insensitive value which did not produce any event at all, or that the patient's condition has actually improved. By means of the present invention, it is also possible to see that, if e.g. five events occurred within a short time frame, but no events were triggered after said time frame, this may be the case in view of the fact that the threshold was adapted after said five events so as to be less sensitive for this special patient. Such statements were not possible on the basis of known trend representations.

The present invention can be used to advantage for monitoring physiological parameters of neonates who are monitored especially with regard to the occurrence of an apnea, a bradycardia and a desaturation. The present invention can, however, also be used for monitoring other physiological parameters of arbitrary patients.

Although the present invention has been described herein before with reference to special embodiments, it is not limited by these embodiments, but only by the appended claims.

We claim:

1. A medical monitoring device comprising:

a monitor for monitoring and recording at least one physiological parameter of a patient;

a comparator for comparing the at least one monitored physiological parameter with a predetermined threshold associated with the respective physiological parameter or a fixed alarm limit associated with the respective physiological parameter, and for detecting the presence of an event in response to the physiological parameter exceeding the associated threshold or the associated alarm limit for a predetermined period of time;

a memory for storing the fact that an event was detected and the parameter value which caused the event, or the parameter value which caused the event and further recorded parameter values, and the respective time at which the event was detected; and a computer arrangement for producing a representation of events, which were stored during a predetermined, preceding period of time, in relation to time, the mode of representation of a respective event depending on the extent to which the parameter causing the event has exceeded the associated threshold or the associated alarm limit, the computer arrangement additionally including a display for displaying the respective thresholds or alarm limits during the predetermined, preceding period of time in relation to time, and the representation for each physiological parameter comprising a coordinate system on a first time axis and on a second axis which extends at right angles to said first axis, the second axis being for a range of values of the respective physiological parameter, the threshold or alarm limit associated with the respective physiological parameter being displayed as a curve in said coordinate system, and the events being shown in the form of bars extending in the direction of said second axis in said coordinate system, the lengths of said bars depending on the maximum extent to which the physiological parameter which caused an event has exceeded the associated threshold or alarm limit.

2. A medical monitoring device according to claim 1, further comprising an input device connected to the medical monitoring device via a user interface, wherein the computer arrangement for producing a representation of the events responds, by means of the input device, to an input carried out by the user to produce said representation.

3. A medical monitoring device according to claim 1, wherein the computer arrangement for producing the representation of the events updates the representation of the events whenever a new event is detected.

4. A medical monitoring device according to claim 1, wherein the memory stores in response to the occurrence of an event the physiological parameter or a plurality of physiological parameters in a predetermined time window before and after the time at which an event has been detected, and wherein the mode of representation of the events depends on the maximum extent to which the parameter causing an event has exceeded the associated threshold or the associated alarm limit within said time window.

5. A medical monitoring device according to claim 4, wherein the computer arrangement produces a time window representation of said one parameter or said plurality of parameters stored during the predetermined time window which is associated with an event.

6. A medical monitoring device according to claim 5, further comprising an input device connected to the medical monitoring device via a user interface, a cursor adapted to be used on the representation via the input device for permitting a user to select a specific event, the computer arrangement being arranged for producing a representation of said parameter or said plurality of parameters in said timewindow in response to the selection carried out by the user.

7. A medical monitoring device according to claim 6, wherein the representation additionally includes a time field containing alphanumeric data defining the date and the time of day at which an event selected by the user occurred.

8. A medical monitoring device according to claim 5, wherein the representation additionally includes an information field for each physiological parameter, which, when an event has been selected by a user, contains alphanumeric data defining the maximum exceeding parameter value that occurred in the time window of the selected event and of the threshold or alarm limit that is valid for this parameter.

9. A medical monitoring device according to claim 1, wherein the computer arrangement is arranged for blanking the display of a threshold or an alarm limit of a physiological parameter during time ranges in which no effective threshold or alarm limit for the parameter exists.

10. A medical monitoring device according to claim 1, wherein the individual thresholds are adapted to be set by a user by an input device which is connected to the medical monitoring device via a user interface.

11. A medical monitoring device according to claim 1, wherein the thresholds correspond to alarm limits, an alarm being triggered by the medical monitoring device in response to (a) said alarm limits being exceeded and (b) said medical monitoring device being placed in an alarm state by an input of an input device.

12. A medical monitoring device according to claim 1, wherein the representation additionally includes a field having alphanumeric data indicative of the total number of events stored in the preceding period of time, and information indicating which physiological parameter has caused how many events.

13. A medical monitoring device according to claim 1, wherein said at least one monitored physiological parameter includes a desaturation of the breath, a respiratory standstill and/or a bradycardia of a neonate.

14. A medical monitoring device according to claim 1, wherein the at least one monitored physiological parameter is compared with the predetermined threshold or the alarm limit, and the presence of an event is detected based on the threshold or based on the alarm limit depending on an operation mode selected by a user.

15. A medical monitoring device according to claim 1, wherein the alarm limit is set by a user.

16. A method of medical monitoring comprising the steps of:

monitoring and recording at least one physiological parameter of a patient;

comparing the at least one monitored physiological parameter with a predetermined threshold associated with the respective physiological parameter or an alarm limit associated with the respective physiological parameter, and detecting the presence of an event, in response to a physiological parameter exceeding the associated threshold or the associated alarm limit for a predetermined period of time;

storing the fact that an event was detected and the parameter value which caused the event, or the parameter value which caused the event and further recorded parameter values, and the respective time at which the event was detected; and producing a representation of the events, which were stored during a predetermined, preceding period of time, in relation to time, the mode of representation of a respective event depending on the extent to which the parameter causing the event has exceeded the associated threshold or the associated alarm limit, during the step of Producing the representation of the events, displaying the respective thresholds or alarm limits during the predetermined, preceding period of time in relation to time, and representing each physiological parameter on a coordinate system having a first axis displaying time and a second axis which extends at right angles to said first axis, the second axis displaying a range of values of the respective physiological parameter, displaying the threshold or alarm limit associated with the respective physiological parameter as a curve in said coordinate system, and displaying the events in the form of bars extending in the direction of the second axis in said coordinate system, the length of said bars depending on the maximum extent to which the physiological parameter which caused an event has exceeded the associated threshold or alarm limit.

17. A method of medical monitoring according to claim 16, wherein the step of producing a representation of the events comprises updating the representation whenever a new event is detected.

18. A method of medical monitoring according to claim 16, wherein the step of storing comprises storing in response to the occurrence of an event the physiological parameter a plurality of physiological parameters in a predetermined time window before and after the time at which an event has been detected.

19. A method for medical monitoring according to claim 16, wherein the alarm limit is set by a user.

* * * * *